(12) United States Patent
Jin

(10) Patent No.: US 11,241,468 B2
(45) Date of Patent: Feb. 8, 2022

(54) METHOD FOR EXTRACTING BIOACTIVE INGREDIENT AND BIOACTIVE INGREDIENT OBTAINED THEREBY

(71) Applicant: Xiangfan Jin, Beijing (CN)

(72) Inventor: Xiangfan Jin, Beijing (CN)

( * ) Notice: Subject to any disclaimer, the term of this patent is extended or adjusted under 35 U.S.C. 154(b) by 197 days.

(21) Appl. No.: 16/492,951

(22) PCT Filed: Jan. 22, 2019

(86) PCT No.: PCT/CN2019/072692
§ 371 (c)(1),
(2) Date: Sep. 11, 2019

(87) PCT Pub. No.: WO2020/150898
PCT Pub. Date: Jul. 30, 2020

(65) Prior Publication Data
US 2021/0100861 A1  Apr. 8, 2021

(51) Int. Cl.
*A61K 36/00* (2006.01)
*A61K 36/185* (2006.01)

(52) U.S. Cl.
CPC ........ *A61K 36/185* (2013.01); *A61K 2236/13* (2013.01); *A61K 2236/37* (2013.01)

(58) Field of Classification Search
CPC .................. A61K 2236/13; A61K 2236/37
See application file for complete search history.

(56) References Cited

U.S. PATENT DOCUMENTS 9,744,200 B1 * 8/2017 Tucker ............... B01D 11/0288
2018/0296616 A1   10/2018 Rivas
2018/0296617 A1 * 10/2018 Rivas ................... B01D 3/108

FOREIGN PATENT DOCUMENTS

| CN | 104277917 A |   | 1/2015 |
| --- | --- | --- | --- |
| CN | 105169726 A |   | 12/2015 |
| CN | 204910807 U |   | 12/2015 |
| CN | 105998713 A | * | 10/2016 |
| CN | 107205960 A |   | 9/2017 |
| CN | 109862901 A |   | 6/2019 |

OTHER PUBLICATIONS

Elsohly, M. A., Slade D., "Chemical constituents of marijuana: The complex mixture of natural cannabinoids", Life Science 78 (2005) 539-548.

* cited by examiner

*Primary Examiner* — Qiuwen Mi
(74) *Attorney, Agent, or Firm* — Bayramoglu Law Offices LLC

(57) ABSTRACT

A method of extracting a bioactive ingredient, including the following steps: step 1) heating a pre-treated fresh cannabis raw material in a vacuum state; step 2) cooling an upper part of the raw material; step 3) collecting a liquid formed in step 2) and containing a bioactive substance; step 4) dispensing and storing the collected liquid containing the bioactive substance.

6 Claims, 2 Drawing Sheets

METHOD FOR EXTRACTING BIOACTIVE INGREDIENT AND BIOACTIVE INGREDIENT OBTAINED THEREBY

CROSS REFERENCE TO THE RELATED APPLICATIONS

This application is the national phase entry of International Application No. PCT/CN2019/072692, filed on Jan. 22, 2019, the entire contents of which are incorporated herein by reference.

TECHNICAL FIELD

The present invention relates to the technical field of substance extraction, and particularly to a method for extracting a bioactive ingredient.

BACKGROUND

*Cannabis*, as a plant of the genus *Cannabis* of the family cannabis, is an annual herb and mostly dioecious. *Cannabis* is cultivated (or wild) all over the world. It is mainly distributed in Asia and Europe. *Cannabis* has a long cultivation history in China and rich in germplasm resources. Since cannabis plants contain a hallucinogenic addiction ingredient, tetrahydrocannabinol (THC), it has long been one of drugs spread unchecked in the Western countries.

*Cannabis* mainly contains components such as cannabinoids, flavonoids, terpenoids, terpenoids, lignans and alkaloids. Among them, cannabinoids are a class of secondary metabolites containing molecular structures of alkyl and monoterpene groups unique to cannabis plants. At present, more than 70 kinds of cannabinoids have been isolated from cannabis dry matter and fresh cannabis leaves (Elsohlyand Slade, 2005), mainly including tetrahydrocannabinol (THC), cannabidiol (CBD), and cannabichromene (CBC), cannabinol (CBN), cannabigerol (CBG) and its propyl homologs THCV, CBDV, CBCV and CBGV, among which THC and CBD are the highest in content.

In 1964, Israeli scientist Raphael Mechoulam first extracted the main component of cannabis, Tetrahydrocannabinol (THC), and proposed the famous cannabis "entourage effect", which is the total effect of all cannabis components. That is, all cannabinoids in cannabis need one another to work normally, which is evolved from natural growth (it is the same with THC and CBD).

To date, pharmaceutical companies based on cannabis-developed products have generally attempted to separate individual chemical substances from plants, but Professor Raphael Mechoulam strongly suspects this and believes that in some cases, a pretty much greater efficacy is achieved in a way that these substances work synergistically with other components of cannabis. He called it an entourage effect, or companion effect, and this is one of the many mysteries about cannabis that needs to be further researched according to him. THC and CBD only touch the skin of cannabis, and the "entourage effect" may bring about a revolution, and it is very likely to find a certain association between cannabinoids and all human diseases.

A source of the odor of cannabis is mainly hundreds of cannabis terpenes. The US Food and Drug Administration (FDA) generally recognizes that cannabis terpenes are safe, cannabis terpenes can greatly enhance the mental effects of cannabis in what is called "entourage effect", and that cannabis terpenes have a strong medical value:

The principle of interaction between cannabis terpenes and an endocannabinoid system is similar to that of cannabinoids. When inhaled or ingested, cannabis terpenes can penetrate the blood-brain barrier and act as an adjunct to cannabinoids.

Terpenes are basic components of complex plant hormones and molecules, pigments, sterols and even cannabinoids. Most notably, terpenes are responsible for the pleasant or less pleasant aroma of cannabis and the physiological effects associated with them.

Studies have shown that cannabinoids act on cannabinoid receptors and neurotransmitters and are easy to bind or dissolve with lipids or fats. Therefore, they may act as inhibitors of serotonin uptake, enhance the activity of norepinephrine (similar to antidepressants), increase the activity of human dopamine, enhance GABA (non-protein amino acids), increase cerebral blood flow and cortical activity, reduce respiratory pathogens and provide anti-inflammatory benefits.

A traditional method of extracting cannabis is to pick flowers on female plants of cannabis, tender leaves at the tip, petals and resin cream attached at positions such as branches of cannabis as raw materials, dry them under sunlight, grind them into fine powder, gather the fine powder into balls or directly mix the fine powder with tobacco to form hemp cigarettes or form an extract. There are also chemical methods such as solid phase extraction and liquid-liquid extraction to extract a single component of cannabis, such as cannabidiol (CBD), cannabinol (CBC) and cannabinol (CBN). These traditional methods all use dried cannabis as a raw material, and most of the active ingredients are lost. Furthermore, a chemical method is employed for extraction, and chemical residues are inevitable, resulting in existence of problems such as impure extraction and a low extraction rate of single components. According to a conventional distillation method, only volatile components can be extracted from the cannabis, and water-soluble components and fat-soluble components cannot be obtained. According to a method of obtaining an extract by using an organic solvent for extraction, various agricultural residues and heavy metals cannot be removed.

SUMMARY

Objective drawbacks of the prior art lie in that dry materials of cannabis are selected as the raw material and most active ingredients therein get lost, and in that chemical residues are evitable when a chemical method is employed for extraction, so that the extracted components are impure and the extraction rate of a single component is low. Therefore, the present invention provides the following technical solutions:

A method of extracting a bioactive ingredient, comprising the following steps:

Step 1) heating the pre-treated fresh cannabis raw material in a vacuum state; heating to make volatile components, water-soluble components and fat-soluble components in the fresh cannabis evaporate into a gaseous state, the vacuum state causing cells of the cannabis to puff, to ensure substances in the cells of the cannabis are replaced out to a maximum degree;

Step 2) cooling an upper part of the raw material; a low temperature in an upper part and a high temperature in a lower part form a convection, so that gases evaporated from the cannabis constantly perform a vaporization-liquefaction circulation;

Step 3) collecting the liquid formed by the step 2) and containing the bioactive substance; since no chemical method is used, the collected liquid does not contain pesticide residues and heavy metals;

Step 4) dispensing and storing the collected liquid containing the bioactive substance; the dispensing and storing can ensure the consistency of the quality of the liquid.

Preferably, the pretreatment of the fresh cannabisraw material in step 1) comprises washing the selected fresh cannabis raw material with clean water and then standing for ultraviolet disinfection.

Preferably, in step 1), the fresh cannabis is placed in a vacuum negative pressure device for heating and depressurization, and a material bin of the vacuum negative pressure device is cleaned and disinfected before the fresh cannabis is placed.

Preferably, the vacuum state in step 1) is 650 to 750 torr.

Preferably, a pressure drop to a vacuum state in step 1) needs to be completed within 3 hours.

Preferably, in step 2), after the raw material is heated for 3 hours, the cooling device is activated to cool an upper part of the raw material.

Preferably, the pressure of the device is kept constant while the cooling device cools the upper part of the device.

Preferably, the liquid in step 3) comprises full spectrum cannabinoids, cannabis terpenes, essential oils, and water from inside the body of cannabis.

Preferably, the liquid dispensed and stored in the step 4) is stored at a room temperature.

The present invention further relates to a bioactive ingredient obtained using the above method.

DETAILED DESCRIPTION OF THE EMBODIMENTS

The present application is further described in detail below with reference to the figures, but the detailed description is not to be construed as limiting the present application.

Figure 1:
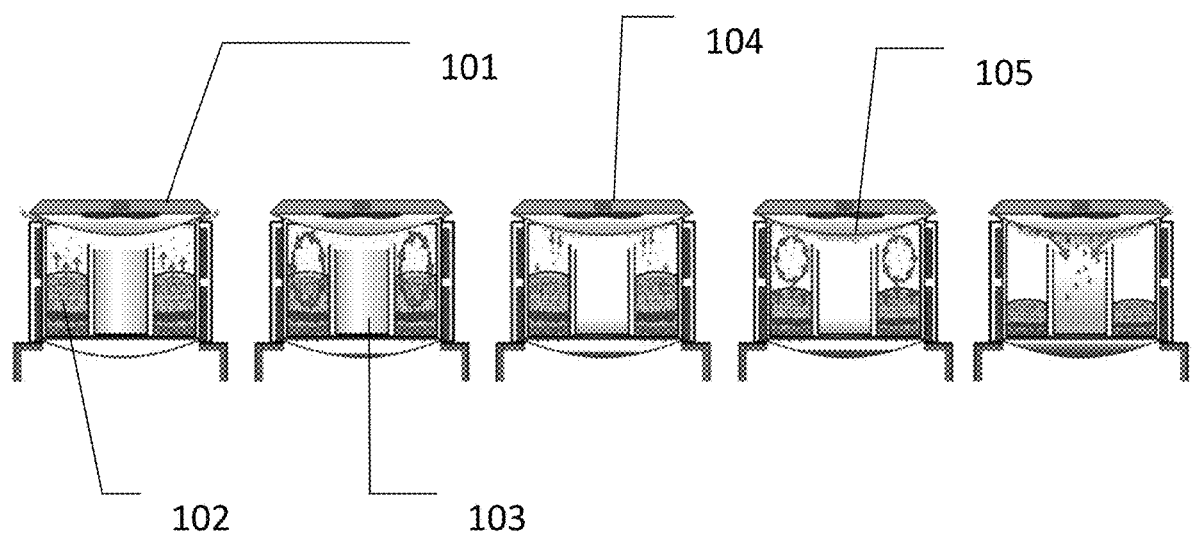
FIG. 1 is a schematic diagram of extracting bioactive ingredients from fresh cannabis according to the present invention.

FIG. 1 shows a principle and process of extracting bioactive components from fresh cannabis according to the present invention. 101 denotes a vacuum negative pressure device, and a material bin of the vacuum negative pressure device 101 is cleaned and disinfected before use. 102 denotes fresh cannabis. 103 denotes a collecting barrel for collecting a liquid containing bioactive substances formed by condensation. 104 denotes a cooling fan at a top of the vacuum negative pressure device. 105 denotes a curved-surface cover below the cooling fan to cool steam to form droplets.

Figure 2:
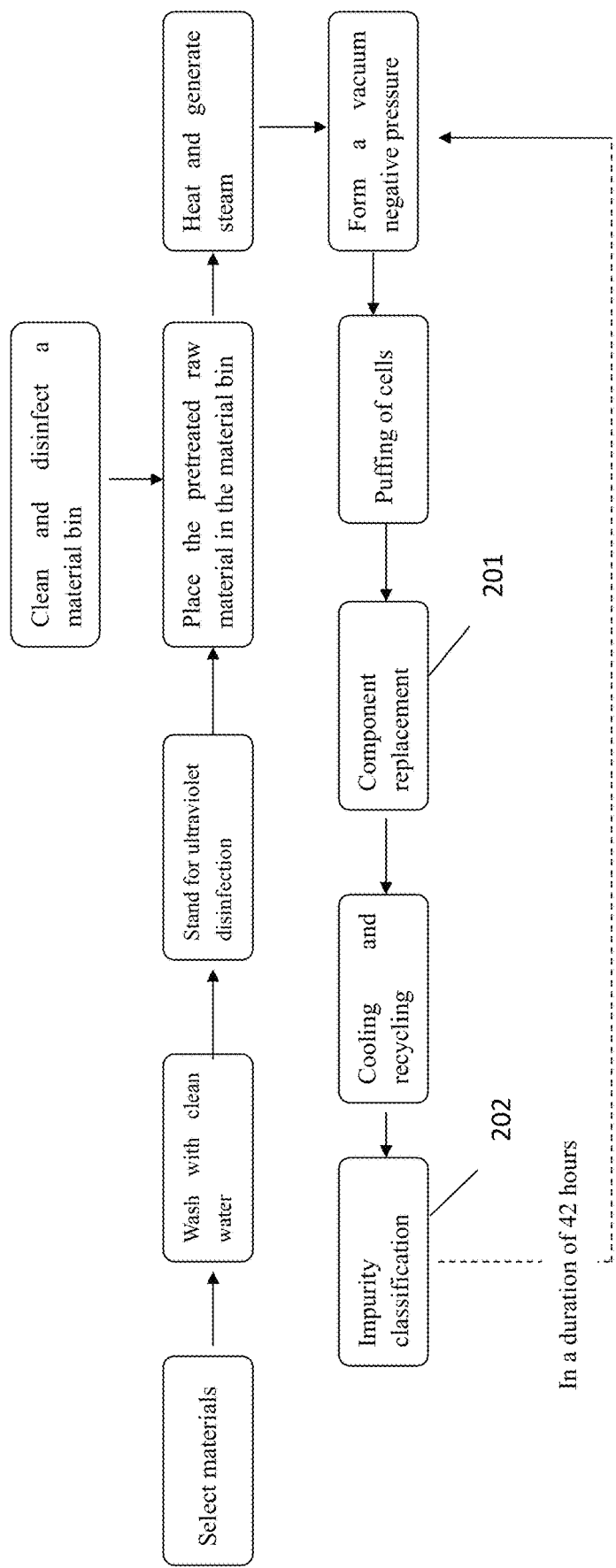
FIG. 2 is a flow chart of a process according to the present invention.

FIG. 2 is a flow chart of a process according to the present invention, wherein block 201 component replacement means that volatile components, the water-soluble components and fat-soluble components in the fresh cannabis raw material are respectively evaporated to form droplets on the curved-surface cover 105 below the cooling fan, and block 202 indicates that a liquid is obtained. Since the present invention does not include a chemical extraction process, the liquid does not contain residues such as pesticides.

Before the fresh cannabis raw material 102 is placed in the vacuum negative pressure device 101, it is washed clean with clean water and kept standing to let water drain, and undergoes ultraviolet disinfection. The material bin of the vacuum negative pressure device 101 is then cleaned and disinfected.

The pretreated fresh cannabis raw material 102 (with 8 kg as a reference) is placed in the vacuum negative pressure device 101, an air ingress valve of the vacuum negative pressure device 101 is closed, and the device 101 is activated for heating. The device 101 is provided with a first temperature and a second temperature, the first temperature is set to 230° C. for 37 hours, and the second temperature is set to 190° C. for 5 hours.

During the heating process of the device 101, the pressure of the device is simultaneously reduced. It is required that the pressure of the device is reduced to a vacuum state of 650 to 750 torr after heating for 3 hours, then the cooling fan 104 is activated until the heating of the device is finished after 42 hours, and the pressure of the device 101 needs to be kept constant while the cooling fan 104 cools the device 101.

After the cannabis raw material 102 is heated, steam is generated. Since the cooling fan 104 at the top is activated to cause the temperature in the upper portion to be low, the steam rises to the curved-surface cover 105 below the cooling fan 104 and then forms droplets, which drip into the collecting barrel in the middle of the device 103. The high temperature in the upper part and a low temperature in the lower part will form a convection, so the circulation of steam evaporation and condensation is constantly performed. At the same time, the vacuum negative pressure environment of the device can ensure the puffing of cannabis cells, so that the cell liquid flows out to ensure volatile substances in the cannabis are replaced to a maximum degree. Under a vacuum negative pressure condition, the originally dense cell structure becomes loose, and even at a lower temperature, the tissue liquid in the cannabis can still be vaporized. Volatile components, fat-soluble components and water-soluble components in cannabis are gradually extracted along with constant vaporization, puffing and component dissolution, and due to internal pressure in a vacuum negative pressure state.

After the operation of the device is completed, the air ingress valve is opened, and the collecting barrel 103 is taken out. The barrel contains a liquid containing bioactive components in the cannabis, the liquid including full spectrum cannabinoids, cannabis terpenes, essential oils, alkanes, nitrogen-containing compounds, amino acids, sugar, aldehydes, alcohols, ketones, flavonoids, glycosides, vitamins and water from inside the body of cannabis.

Finally, the liquid is dispensed and stored and placed at a room temperature.

After a nuclear magnetic resonance (NMR 600 Hz) test is performed multiple times, a peak width at half height of the finally-extracted liquid according to the present invention is in a range of 44-55 Hz, smaller by a half than ordinary small-molecule water (80-100 Hz), and the liquid is more easily absorbed by the human body.

As compared with the prior art, the present invention ① solves the problem that the traditional cannabis process uses the dry material as the raw material, and most of active ingredients therein get lost, and the problem that chemical residues are evitable when a chemical method is employed for extraction, so that the extracted components are impure and insufficient, and instead, the present invention can provide extraction of full components of cannabis in a simple, convenient, quick, full-component, high-concentrated, professional and stable manner, to facilitate absorption by the human body to its full.

②the present invention solves the problem that the original chemical method cannot thoroughly solve the uniformity, stability and water resistance of liquid-state mixing of multiple phases such as water solubility, fat solubility and volatility of cannabis. The cannabis scent itself is an ultrafine molecular group. The nuclear magnetic resonance NMR test is performed for a small molecular group at about 49 Hz, and about 5 to 6 water molecules form a molecular cluster. Because the molecular group is small enough, the three forms that cannot be easily polymerized can fused and polymerized together with one another.

③the present invention provides a pure physical technique: the special physical phenomenon that a vacuum negative pressure causes molecular bond rupture causes the liquid to change from a macromolecular group to a small molecular group, which increases the contact interface between molecules, and is highly beneficial to polymerization or decomposition of liquids of various liquid phases. The molecular bond is broken, so that the molecular bond lengths of the heterogeneous liquids tend to be the same, thereby promoting the sufficient polymerization of the heterogeneous liquids which are originally difficult to fuse.

④The present invention has characteristics such as high extraction efficiency, low extraction cost, and high repeatability and consistency of components before and after extraction. With this technology, the plant extraction standard can be perfectly realized. The maximal extraction effect is reflected by extracting all-ingredient concentrated essence to maximize the efficacy of cannabis.

Although embodiments of the present invention have been shown and described, it may be understood that the above embodiments are illustrative and are not to be construed as limiting the scope of the present invention. Those having ordinary skill in the art may make changes, modifications, substitutions and variations to the above embodiments within the scope of the present invention.

What is claimed is:

1. A method of extracting a bioactive ingredient, comprising the following steps:

step 1) heating a fresh cannabis raw material after being subjected to a pretreatment in a vacuum state;

step 2) cooling an upper part of the fresh cannabis raw material;

step 3) collecting a liquid formed in the step 2), wherein the liquid contains a bioactive substance; and step 4) dispensing and storing the liquid containing the bioactive substance;

wherein the pretreatment of the fresh cannabis raw material in the step 1) comprises washing the fresh cannabis raw material with clean water and then keeping the fresh cannabis raw material for ultraviolet disinfection;

wherein in the step 1), the fresh cannabis raw material is placed in a vacuum negative pressure device for heating and depressurization, and a material bin of the vacuum negative pressure device is cleaned and disinfected before the fresh cannabis raw material is placed;

wherein the vacuum state in the step 1) is 650 torr to 750 torr.

2. The method of extracting the bioactive ingredient according to claim 1, wherein a pressure drop to the vacuum state in the step 1) is completed within 3 hours.

3. The method of extracting the bioactive ingredient according to claim 2, wherein in the step 2), after the fresh cannabis raw material is heated for 3 hours, a cooling device is activated to cool the upper part of the fresh cannabis raw material.

4. The method of extracting the bioactive ingredient according to claim 3, wherein a pressure in the cooling device is kept constant while the cooling device cools the upper part of the fresh cannabis raw material.

5. The method of extracting the bioactive ingredient according to claim 4, wherein the liquid in the step 3) comprises full spectrum cannabinoids, cannabis terpenes, essential oils, and water from inside a body of cannabis from the fresh cannabis raw material.

6. The method of extracting the bioactive ingredient according to claim 5, wherein the liquid dispensed and stored in the step 4) is stored at a room temperature.

* * * * *